United States Patent [19]

Pakhomov et al.

[11] 4,436,720

[45] Mar. 13, 1984

[54] GRANULATED TREATMENT-AND-PROPHYLACTIC DENTAL PREPARATION POSSESSING ANTICARIOUS EFFECT

[76] Inventors: Gennady N. Pakhomov, Leninsky prospekt 123/1, kv. 529, Moscow; Anita Y. Luste, ulitsa Lachplesha 27, kv. 22; Galina I. Kadnikova, ulitsa Ya. Rudzutaka 60, kv. 10, both of Riga; Anatoly G. Kolesnik, ulitsa Shosseinaya 58 korpus 2, kv. 59, Moscow, all of U.S.S.R.

[21] Appl. No.: 472,166

[22] Filed: Mar. 4, 1983

[51] Int. Cl.$^3$ .......................... A61K 7/16; A61K 7/18; A61K 7/26; A61K 9/46

[52] U.S. Cl. ........................................ 424/44; 424/52; 424/57; 424/95

[58] Field of Search ...................... 424/44, 52, 57, 95

[56] References Cited

U.S. PATENT DOCUMENTS

| | | | |
|---|---|---|---|
| 1,082,681 | 12/1913 | Danner | 424/49 |
| 1,225,362 | 5/1917 | Ruthruff | 424/57 |
| 1,262,888 | 4/1918 | Westlake | 424/44 |
| 1,297,494 | 3/1919 | Rhein | 424/44 |
| 1,664,182 | 3/1928 | Parisi | 424/95 |
| 2,128,917 | 9/1938 | Crocker | 424/49 |
| 2,154,168 | 4/1939 | Klein et al. | 424/57 |
| 3,087,857 | 4/1963 | Davis et al. | 424/44 |
| 3,458,397 | 7/1969 | Myers et al. | 424/95 |
| 3,735,002 | 5/1973 | Poston | 424/95 |
| 3,962,417 | 6/1976 | Howell | 424/44 |

*Primary Examiner*—Shep K. Rose
*Attorney, Agent, or Firm*—Burgess, Ryan and Wayne

[57] ABSTRACT

A granulated treatment-and-prophylactic dental preparation possessing anti-caries effect which comprises an abrasive substance, tartaric acid, sodium bicarbonate, a foaming agent, a flavoring agent, a binder and an anticarious substance comprising a product obtained by treatment of bone tissue with a diluted mineral acid till a complete dissolution of mineral components and water-soluble proteins contained in the bone tissue, separation of the resulting solution, dilution it with water added with a stabilizing agent citric acid or salts thereof, followed by neutralization of the solution and drying, and containing the following components, percent by weight:

Calcium—2 to 6.
Sodium—19 to 23.
Potassium—0.04 to 0.18.
Mineral acid anion—6 to 10.6.
Orthophosphoric acid anion—1.5 to 5.0.
Water-soluble proteins—1.0 to 5.0.
Magnesium—0.05 to 0.2.
Mixture of trace elements including fluorine, manganese, tin, zinc, iron—0.01 to 0.02.
Complex citrates compounds as calculated for citric acid anion—the balance;

and having the following proportions of the starting components, percent by weight:

Tartaric acid—11 to 15.
Foaming agent—1.8 to 2.27.
Sodium bicarbonate—42 to 46.
Binder—0.11 to 0.13.
Flavoring agent—0.8 to 1.2.
Substance possessing anti-caries effect—1 to 6.
Abrasive substance—the balance.

3 Claims, No Drawings

GRANULATED TREATMENT-AND-PROPHYLACTIC DENTAL PREPARATION POSSESSING ANTICARIOUS EFFECT

FIELD OF THE INVENTION

The present invention relates to stomatology and, more specifically, to a treatment-and-prophylactic granulated dental preparation possessing anti-caries effect which is useful for everyday hygiene of the oral cavity, as well as for ensuring antiinflammatory effect in periodontal diseases and anesthetic effect in hyperesthesia of hard dental tissues.

BACKGROUND OF THE INVENTION

Known in the art are various treatment-and-prophylactic dental preparations: tooth pastes, elixirs, gels, powders.

In some cases, due to liability of powders to dusting, they are replaced by pastes. Nevertheless, at the present time attempts are still being made to develop dry therapeutical preparations for hygiene and care of the oral cavity.

Known in the art is a treatment-and-prophylactic foaming preparation for everyday tooth cleaning possessing a certain preventive activity against peridontal diseases and caries which is available in a granulated form (under the tradename of "Merfluan" produced by W. Millck, FRG). "Merfluan" comprises a granulate having no odour, readily soluble in water with liberation of carbon dioxide. The granulate has the following chemical composition, percent by weight:

Tartaric acid—17,
Mixture of calcium and magnesium carbonates and minor amount of calcium phosphates—8.6,
Foaming agent (sodium salt of ethers of fatty alcohols and sulphuric acid)—7.7,
Sea salt—7.9,
Extract from 1 g of myrrh gum and sodium bicarbonate—the balance.

Owing to a specific granulation process, each granule of the preparation contains all the components in predetermined proportions in a concentrated form.

A disadvantage of this prior art preparation resides in a low value of its anti-caries and cleaning effects. Furthermore, granules of this prior art preparation has a high abrasive effect and very low mechanical strength.

SUMMARY OF THE INVENTION

It is the main object of the present invention to provide a granulated treatment-and-prophylactic dental composition possesses an increased anti-caries effect.

It is another object of the present invention to provide a granulated treatment-and-prophylactic dental preparation which features granules with reduced abrasive characteristics and high mechanical strength.

The objects of the present invention are accomplished by a granulated treatment-and-prophylactic dental preparation possessing anti-caries effect comprising an abrasive substance, tartaric acid, sodium bicarbonate, a foaming agent, a binder and additionally containing, according to the present invention, an anti-caries substance which comprises a product prepared by treatment of bone tissue with a dilute mineral acid to achieve complete dissolution of mineral components and water-soluble proteins contained in the bone tissue, separation of the resulting solution, dilution thereof with water with the addition of a stabilizing agent—citric acid or salts thereof, followed by neutralization of the solution and drying. The anti-caries substance contains the following components, in percent by weight:

calcium—2 to 6,
sodium—19 to 23,
potassium—0.04 to 0.18,
mineral acid anion—6 to 10.6,
orthophosphoric acid anion—1.5 to 5.0,
water-soluble proteins—1.0 to 5.0,
magnesium—0.05 to 0.2,
mixture of trace elements including fluorine, manganese, tin, zinc, iron—0.01 to 0.02,
complex citrate compounds as calculated for citric acid anion—the balance, at the following proportions of the starting components, percent by weight:

tartaric acid—11 to 15,
foaming agent—1.8 to 2.7,
sodium bicarbonate—42 to 46,
binder—0.11 to 0.13,
flavouring agent—0.8 to 1.2,
anti-caries-effect substance—1 to 6,
abrasive substance—the balance.

To ensure a long-time storage of the granulated treatment-and-prophylactic dental preparation according to the present invention, it is desirable that it additionally contain sodium sulphate in an amount of from 1.9 to 2.1% by weight.

It is advisable that the granulated dental preparation according to the present invention contain, as the abrasive substance, dicalciumphosphate dihydrate.

DETAILED DESCRIPTION OF THE INVENTION

The dental preparation according to the present invention is in the form of granules with a size of from 0.15 to 1.5 mm having white color, a pleasant odor and taste which remain unchanged upon storage for one year. The preparation according to the present invention has high anti-caries characteristics owing to the fact that it incorporates a substance possessing anticarious effect. At a content of the anti-caries substance in the composition according to the present invention in an amount of below 1.0%. by weight or above 6.0% by weight the treatment-and-prophylactic properties of the granulate are lowered.

The preparation according to the present invention produces the fissure caries reduction by 35%, whereas the prior art granulated preparation "Merfluan"—only by 17%.

The dental preparation according to the present invention has good cleaning properties which is proven by statistically significant reduction of oral hygiene index (OHI-S). The dental composition according to the present invention has lowered abrasive properties (by 20% as compared to the prior art preparation "Merfluan"), while retaining its high cleaning properties. The dental calculus is dissolved by the preparation according to the present invention by 30%.

The dental preparation according to the present invention is used in the following manner. From a flask with granules the latter are poured onto a preliminarily wetted tooth brush and teeth are cleaned as usual. During the tooth cleaning the granulate contacts water and the preparation rapidly dissolves with evolution of carbon dioxide. At the same time an intensive foaming takes place which ensures fixation of carbon dioxide on the dental and gingival surfaces which causes dissolution of the dental calculus. The dental composition according to the present invention and the anti-caries substance incorporated therein have been tested in experiments on animals and on patients in clinics. A 3% solution of the anti-caries substance has been tested in comparison with the control. The tests were carried out on 80 Wistar rats aged one months (40 animals for the test solution and 40—control group). All animals were given the cariogenic Stephan 580 diet and the test solutions were applied to the teeth for 3 minutes every day during 4 weeks of the experiment. On completion of the experiment the teeth were extracted and the caries index was determined following a generally-accepted procedure. The data obtained in the experiment are shown in Table 1 hereinbelow.

TABLE 1

Comparative data on anti-caries efficiency of a solution of the anti-caries substance according to the present invention and the control

| Preparation (group) | Characteristics | | | | | |
|---|---|---|---|---|---|---|
| | Fissures | | Contact zones | | Total in all zones | |
| | Caries index | Anti-caries efficiency, % | Caries index | Anti-caries efficiency, % | Caries index | Anti-caries efficiency, % |
| Control group | 26.75 | — | 2.76 | — | 29.51 | — |
| Solution of the anti-caries substance according to the present invention | 20.42 | 23.7 | 1.00 | 63.7 | 21.42 | 27.4 |

The caries-preventing efficiency of the dental preparation possessing anti-caries effect according to the present invention in the form of a 3% solution for applications when administered for a period of not less than 1.5 years with the administration schedule of 2 times monthly on children aged 7-10 years is, according to the characteristic of a relative reduction of the caries increment as shown by DMF-T index, from 44.1 to 53.7% and according to DMF-S index—from 40.2 to 58.0%. At the same time, according to the data of CRT test, the acid resistance of the enamel is substantially increased.

It has been found that the efficiency of a 3% solution of the anti-caries substance according to the present invention is high in early stages of dental caries treatment; the positive result of the treatment manifests in disappearance or reduction of demineralization spots; it is observed in 72.4-84% of cases, stabilization of the process—in 14-31.9% and lack of therapeutic effect—in 2-8% of the studied cases.

Efficiency of a 3% solution of the anti-caries-effect substance according to the present invention in the treatment of hyperesthesia of hard dental tissues is good; fully increased sensitivity of tooth necks is removed in 23.2-36.4% of the cases.

Clinical studies of the anti-caries substance were carried out to find out its prophylactic effect on children and pregnant women, as well as to evaluate its efficiency in the conservative treatment of focal demineralizations of dental enamel. The anti-caries substance was used as 1.5-3% solutions for applications.

In accordance with the results of epidemiological studies 176 children aged 7-8 years were chosen. The children were divided into two groups:

Group I—children to whom the anticarious solution was applied—81 persons;

Group II—control group of children—95 persons.

Applications of the solution were effected after a preliminary tooth cleaning with a hygienic tooth paste. Then teeth were protected from saliva by means of lignine tampons and dried by air jet. By means of spoons made of a flexible plastic, whereinto abundantly wetted cotton wool tampons were placed, the solution was applied onto all dental surfaces. The duration of applications was 10 minutes on each jaw. After applications the children were advised to abstain from taking meals and drinking for two hours. All subsequent applications were conducted following this procedure one in two weeks.

The primary examination of the oral cavity revealed a relatively uniform level of caries attack evaluated as $1.12 \pm 0.13$ to $1.30 \pm 0.13$ in terms of DMF-T index.

The results of the use of the anti-caries solution according to the present invention are shown in Table 2.

It follows from the Table that the reduction of caries increment in Group 1 of the children was 44.7 and 49.5% in terms of DMF-T and DMF-S indices respectively.

In the analysis of the cariostatic effect of the test substance relative to individual groups of teeth its effect was revealed on both first molars already erupted by the beginning of the investigation and in relation to incisors erupted during the observation period.

The solution of the test substance was employed for the treatment of dental demineralization in 81 schoolchildren aged 7 to 14 years.

The children were divided into two subgroups depending on the form of demineralization:

Groups 3a—children with slowly-progressing demineralization (42 schoolchildren altogether);

Group 3b—children with rapidly-progressing demineralization (39 schoolchildren altogether).

In general, demineralization was observed on 229 teeth of the children of 3a group and on 248 teeth of the children of 3b group (see Table 3). The control groups were the same groups of children as in the previous experiment which were identified as Groups Ia and Ib.

To attain a positive result in the treatment of teeth by a solution of the test substance, it was necessary to carry out 10-15 applications on the average in group 3a and 20-25 applications in group 3b.

TABLE 2

| | | Dynamics of dental caries intensity during the disease | | | | | | | | | |
|---|---|---|---|---|---|---|---|---|---|---|---|
| | Character of performed preventive measures | Characteristics after 1 year of observation | | | | | Characteristics after three years of observation | | | | |
| | | Number of examined children | Caries increment | | Reduction of increment | | Number of examined children | Caries increment | | Reduction of increment, % | |
| Group No. | | | DMF-T | DMF-S | DMF-T | DMF-S | | DMF-T | DMF-S | DMF-T | DMF-S |
| 1 | 2 | 3 | 4 | 5 | 6 | 7 | 8 | 9 | 10 | 11 | 12 |
| 1. | Application | 81 | $0.78 \pm$ | $1.12 \pm$ | 19.6 | 22.7 | 81 | $1.61 \pm$ | $2.59 \pm 0.34$ | 44.7 | 49.5 |

TABLE 2-continued

Dynamics of dental caries intensity during the disease

| Group No. | Character of performed preventive measures | Characteristics after 1 year of observation | | | | | Characteristics after three years of observation | | | | |
|---|---|---|---|---|---|---|---|---|---|---|---|
| | | Number of examined children | Caries increment | | Reduction of increment | | Number of examined children | Caries increment | | Reduction of increment, % | |
| | | | DMF-T | DMF-S | DMF-T | DMF-S | | DMF-T | DMF-S | DMF-T | DMF-S |
| 1 | 2 | 3 | 4 | 5 | 6 | 7 | 8 | 9 | 10 | 11 | 12 |
| | of the remineralizing solution of the test substance on teeth | | 0.16 | 0.28 | | | | 0.18 | | | |
| 2. | Control | 95 | 0.97 ± 0.14 | 1.45 ± 0.24 | — | — | 78 | 2.91 ± 0.16 | 5.13 ± 0.25 | | |

TABLE 3

Number of teeth of Group 3 and Group I (control) children with demineralization foci depending on their size

| Stain size | Number of teeth with demineralization foci | | | |
|---|---|---|---|---|
| | 1a control group | 1b control group | 3a group | 3b group |
| 1 | 2 | 3 | 4 | 5 |
| $2 \text{ mm}^2$ | 73 | 48 | 81 | 24 |
| $2-3 \text{ mm}^2$ | 125 | 102 | 117 | 120 |
| $3 \text{ mm}^2$ | 81 | 155 | 31 | 104 |
| Total number of spots | 279 | 305 | 229 | 248 |

Remineralizing therapy was more efficient in the treatment of a slowly-proceeding demineralization process. Small-size spots (2 and 2-3 mm$^2$) disappeared and reduced in size faster than larger-size spots. The conservative treatment of a rapidly-proceeding dental demineralization in group 3b of children was less effective, but a direct relationship of the treatment efficiency vs. size of spots was retained in this group as well (see Table 4).

A positive effect of the treatment—disappearance of spots—in group 3a was observed on 193 teeth out of 229 (84±2.4%) as compared to the control group, wherein a positive treatment result was noted for 100 teeth out of 270 (36±2.4%).

The process stabilization of Group 3a was noted on 31 teeth (14±6.23%) and on 87 teeth (31±2.8%) in the control group.

Spot size increase and the formation of cavities in Group 3a took place on only 5 teeth out of 229 (2±0.9%) and in the control group—on 92 out of 279 teeth (33±2.8%).

The difference between the parameters of the control group and group 3a are statistically true (see Table 4).

In group 3b the treatment of a rapidly-proceeding demineralization had a positive result on 155 teeth out of 248 (63±3.0%), whereas in the control group a spontaneous disappearance was noticed on 33 teeth out of 305 which constituted only 11±1.8%. On 60 teeth of the children of group 3b (24±2.7%) the process was stabilized. In the zone of dimeneralization foci on 33 teeth of the children of group 3b (13±2.1%) cavities were formed.

The difference between the characteristics of group 3b and the control 1b group is statistically significant (see Table 4).

Therefore, an average positive result in the treatment of rapidly-proceeding and slowly-proceeding dimeneralization of dental enamel was equal to 73.5%.

The solution of the anticarious-effect substance according to the present invention was tested on pregnant women. From the carried out epidemiological studies of the pregnant women it was found out that with extension of the pregnancy period the frequency and intensity of focal demineralization of dental enamel is also increased. To prevent such injuries, in 69 pregnant women (group 1) a solution of the anticarious-effect substance according to the present invention was employed in the form of applications. 64 pregnant women served as the control (group II).

As a result of the study, in women of both groups (1-3 months of pregnancy) there was found a relatively similar level of tooth injury with focal demineralizations—29-30% with 1.8±0.3 teeth injured, on the average basis.

By the end of the pregnancy period in the women of the control group focal demineralizations of dental enamel were in 64% of the cases with the average index of 5.23±0.7 teeth injured.

The use or the anti-caries substance according to the present invention in group I of women has made it possible not only to prevent the formation of novel focal lesions of enamel, but also to stabilize the process in already existing foci (no increase of the demineralization foci size or the formation of cavities was observed).

The granulated dental preparation according to the present invention, as well as placebo granules and granules of the known composition "Merfluan" (produced in FRG) were tested on 100 Wistar rats aged one months (25 animals for each preparation and 25 animals in the control group). The animals were fed with the cariogenic Stephan-580 diet and during the experiment (4 weeks) their teeth were cleaned with each preparation (placebo granules, "Merfluan" granules and granules of the preparation according to the present invention) for 1-1.5 minutes. On completion of the experiment the teeth extracted and the caries index was then determined following a generally-accepted procedure.

TABLE 4

Results of the treatment of children's teeth with a remineralizing solution of the anti-caries-effect substance of the present invention

| | | Characteristic of demineralization foci Distribution of spots in children of group 3a | | | | | |
|---|---|---|---|---|---|---|---|
| | Result of the treatment of deminerali- | According to size | | | According to number | | t as compared to the control |
| Nos | zations of dental enamel | below 2 mm$^2$ | 2–3 mm$^2$ | above 3 mm$^2$ | Abs. | M ± m, % | (p < 0.001) |
| 1 | 2 | 3 | 4 | 5 | 6 | 7 | 8 |
| 2 | Disappearance of spots | 64 | 98 | 31 | 193 | 84 ± 2.4 | 10.8 |
| 3 | Process stabilization | 13 | 18 | — | 31 | 14 ± 2.3 | 4.5 |
| 4 | Formation of defects | 4 | 1 | — | 5 | 2 ± 0.9 | 8.9 |
| 5 | Total | | | | 229 | 100 | |
| 6 | Disappearance of spots | 19 | 73 | 63 | 255 | 63 ± 3.0 | 12.8 |
| 7 | Process stabilization | 1 | 31 | 23 | 60 | 24 ± 2.7 | 3.4 |
| 8 | Formation of defects | 4 | 16 | 13 | 33 | 13 ± 2.1 | 14.7 |
| 9 | Total | | | | 248 | 100 | |

Evaluation of the abrasive effect was carried out on 18 human teeth extracted according to medical indications. The abrasive effect of placebo granules was assumed as unit.

For evaluation of cleaning properties of the compared dental preparations during their clinical approbation there were formed 4 groups of schoolchildren each consisting of 30 patients with approximately similar background characteristics. The schoolchildren cleaned teeth with the test preparations every day under control. The assessment was effected following a standard procedure—in terms of OHI-S index (Greene J. C., Vermillion J. E.—The simplified oral hygiene index, J. Amer. Dent. Ann., 1964, 68, 1, 7–13).

The dissolving (lytic) effect on the dental calculus was evaluated in terms of Silness-Loe index. To this end, in preliminary examinations 30 patients were chosen (10 in each group) with a considerable rate of the formation of solid deposits (dental calculus) on the dental enamel and the same initial values of the Silness-Loe index of about 0.9. For a distinct evaluation of the degree of deposition of dental calculus use was made of an staining preparation Revelor (France).

The results of the tests are shown in Table 5.

A comparative study of the dental granulate "Merfluan" and the dental preparation according to the present invention shows that the anti-caries effect of the latter is by two times higher, abrasive power by 20% lower and lytic effect on dental calculus is by 30% higher than that of the prior art preparation "Merfluan".

TABLE 5

Comparative data of tests of the dental preparation according to the present invention, placebo granules and granules of the known dental preparation "Merfluan"

| | Characteristics | | | |
|---|---|---|---|---|
| Preparation | Anti-caries efficiency, % | Abrasive effect, relative units | Cleaning effect, OHI-index | Lysis of dental calculus (Silness-Loe index) |
| 1 | 2 | 3 | 4 | 5 |
| Placebo granules | 5.0 | 1.0 | 0.94 ± 0.08 | 0.83 ± 0.05 |
| Granules of the known dental composition "Merfluan" | 17.2 | 0.46 | 0.82 ± 0.09 | 0.41 ± 0.03 |
| Dental preparation according to the present invention | 35.4 | 0.35 | 0.61 ± 0.08 | 0.29 ± 0.02 |

As it is seen from the results of the performed tests, the dental preparation prepared according to the present invention is superior to the dental granulate "Merfluan" in all characteristics.

The dental preparation according to the present invention is produced in the following manner. An abrasive agent, an anti-caries substance are mixed with a wetted binder and a foaming agent; the mixture is disintegrated and thoroughly intermixed with tartaric acid, sodium bicarbonate, a flavouring agent and subjected to granulation.

As the abrasive substance use can be made of chalk, dicalciumphosphate dihydrate and other agents. It is preferred to use dicalciumphosphate dihydrate. As the foaming agent use can be made of sodium laurylsulphate, sodium laurylsarcosinate and the like. As the binder gelatine is preferably used. The resulting granulate is screened. For long-time storage, the granulate can be powdered with sodium sulphate. The thus-produced granules are dispensed into flasks. The storage life is one year.

For a better understanding of the present invention some specific examples illustrating different embodiments of the dental composition according to the present invention are given hereinbelow.

EXAMPLE 1

A treatment-and-prophylactic dental preparation possessing anti-caries effect has the following composition, g:

| | | |
|---|---|---|
| anti-caries substance of the following composition, wt. percent: | | |
| calcium | 6.00 | |
| phosphoric acid anion | 5.00 | |
| sodium | 19.00 | |
| magnesium | 0.05 | |
| potassium | 0.04 | 6.00 |
| mineral acid anion (chloride) | 6.00 | |
| mixture of trace elements including fluorine, manganese, tin, zinc, iron | 0.01 | |
| water soluble proteins | 1.00 | |
| complex citrate compounds as calculated for citric acid anion | 63.90 | |
| dicalciumphosphate dihydrate | 31.90 | |
| gelatine | 0.12 | |
| sodium laurylsulphate | 2.00 | |
| tartaric acid | 12.95 | |
| sodium sulphate | 2.00 | |
| flavouring agent | 1.00 | |
| sodium bicarbonate | to 100.00 | |

The granulated treatment-and-prophylactic dental preparation possessing anti-caries effect according to the present invention is obtained in the following manner:

Dicalciumphosphate dihydrate, the anti-caries substance are mixed with wetted gelatine and sodium laurylsulphate. The resulting mixture is disintegrated and thoroughly intermixed with tartaric acid, sodium bicarbonate, the flavouring substance and subjected to granulation. For a long-term storage the granulate is powdered with sodium sulphate. The thus-produced granules are packed into flasks.

The storage period is one year.
Diameter of granules—0.8 mm
Mechanical strength of granules—6.0 kg/cm².

EXAMPLE 2

A granulated treatment-and-prophylactic dental composition possessing anti-caries effect has the following composition, g:

| | | |
|---|---|---|
| anti-caries substance of the following composition, wt. percent: | | |
| calcium | 2.00 | |
| orthophosphoric acid anion | 1.90 | |
| sodium | 23.00 | |
| magnesium | 0.20 | |
| potassium | 0.18 | |
| mineral acid anion (chloride) | 10.60 | 1.00 |
| mixture of trace elements including fluorine, manganese, tin, zinc, iron | 0.02 | |
| water soluble proteins | 5.00 | |
| complex citrate compounds as calculated for citric acid anion | 57.10 | |
| dicalciumphosphate dihydrate | 36.79 | |
| gelatine | 0.11 | |
| sodium laurylsulphate | 1.80 | |
| tartaric acid | 13.00 | |
| sodium sulphate | 2.10 | |
| flavouring agent | 1.20 | |
| sodium bicarbonate | to 100.00 | |

The preparation is produced as described in the foregoing Example 1.

Diameter of granules—1.1 mm,
Mechanical strength of granules—8.8 kg/cm².

EXAMPLE 3

A treatment-and-prophylactic granulated dental preparation possessing anti-caries effect has the following composition, g:

| | | |
|---|---|---|
| anti-caries substance of the following composition, weight percent: | | |
| calcium | 4.00 | |
| orthophosphoric acid anion | 3.92 | |
| sodium | 21.20 | |
| magnesium | 0.14 | |
| potassium | 0.12 | 3.00 |
| mineral acid anion (chloride) | 8.20 | |
| mixture of trace elements | 0.02 | |
| water-soluble proteins | 3.00 | |
| complex citrate compounds as calculated for citric acid anion | 59.40 | |
| dicalciumphosphate dihydrate | 34.90 | |
| gelatine | 0.13 | |
| sodium laurylsulphate | 2.27 | |
| tartaric acid | 11.00 | |
| sodium sulphate | 1.90 | |
| flavouring agent | 0.80 | |
| sodium bicarbonate | to 100.00 | |

The preparation of the above composition is produced in a manner similar to that described in Example 1.

Diameter of granules—1.4 mm
Mechanical strength of granules—9.5 kg/cm².

EXAMPLE 4

A granulated treatment-and-prophylactic dental preparation possessing anti-caries effect according to the present invention has the following composition, g:

| | | |
|---|---|---|
| anti-caries substance of the following formulation, percent by weight: | | |
| calcium | 3.50 | |
| orthophosphoric acid anion | 5.00 | |
| sodium | 20.20 | |
| magnesium | 0.18 | |
| potassium | 0.15 | 4.5 |
| mineral acid anion (chloride) | 7.95 | |
| mixture of trace elements including fluorine, manganese, tin, zinc, iron | 1.10 | |
| complex citrate compounds as calculated for citric acid anion | 61.90 | |
| dicalciumphosphate dihydrate | 33.45 | |
| gelatine | 0.12 | |
| sodium laurylsulphate | 2.25 | |
| tartaric acid | 12.55 | |
| sodium sulphate | 1.70 | |
| flavouring agent | 0.95 | |
| sodium bicarbonate | to 100.00 | |

The composition of the above formulation is prepared following the procedure described in Example 1 hereinbefore.

Diameter of granules—0.95 mm
Mechanical strength of granules—3.8 kg/cm².

EXAMPLE 5

A granulated treatment-and-prophylactic dental preparation possessing anti-caries effect according to the present invention has the following composition, g:

| anti-caries substance of the following formulation, percent by weight: | | |
| --- | --- | --- |
| calcium | 3.20 | |
| orthophosphoric acid anion | 4.90 | |
| sodium | 22.00 | |
| magnesium | 0.18 | |
| potassium | 0.17 | |
| mineral acid anion (chloride) | 8.95 | 5.00 |
| mixture of trace elements including fluorine, manganese, tin, zinc, iron | 0.02 | |
| water-soluble proteins | 1.10 | |
| complex citrate compounds as calculated for citric acid anion | 59.48 | |
| dicalciumphosphate dihydrate | 32.75 | |
| gelatine | 0.12 | |
| sodium laurylsulphate | 2.19 | |
| tartaric acid | 12.20 | |
| sodium sulphate | 2.05 | |
| flavouring agent | 0.90 | |
| sodium bicarbonate | up to 100.00. | |

The preparation according to the present invention is obtained as described in Example 1 hereinbefore.
Diameter of granules—0.7 mm
Mechanical strength of granules—2.3 kg/cm².

EXAMPLE 6

A granulated treatment-and-prophylactic dental preparation possessing anti-caries effect according to the present invention has the following composition, g:

| anti-caries substance of the following formulation, percent by weight: | | |
| --- | --- | --- |
| calcium | 3.80 | |
| orthophosphoric acid anion | 5.00 | |
| sodium | 22.80 | |
| magnesium | 0.20 | |
| potassium | 0.18 | |
| mineral acid anion (chloride) | 8.88 | 1.50 |
| mixture of trace elements including fluorine, manganese, tin, zinc, iron | 0.02 | |
| water-soluble proteins | 1.36 | |
| complex citrate compounds as calculated for citric acid anion | 57.76 | |
| dicalciumphosphate dihydrate | 36.29 | |
| gelatine | 0.11 | |
| sodium laurylsulphate | 1.90 | |
| tartaric acid | 13.00 | |
| flavouring agent | 0.95 | |

| anti-caries substance of the following formulation, percent by weight: | |
| --- | --- |
| sodium bicarbonate | up to 100. |

The preparation of the above-specified composition is prepared in a manner similar to that described in Example 1 hereinbefore.
Diameter of granules—1.20 mm
Mechanical strength of granules—9.0 kg/cm².

What is claimed is:

1. A granulated treatment-and-prophylactic dental preparation comprising an abrasive substance, tartaric acid, sodium bicarbonate, a foaming agent, a flavouring agent, a binder and an anticarious substance comprising a product obtained by treatment of a bone tissue with dilute mineral acid to complete dissolution of mineral components and water-soluble proteins contained in the bone tissue, separation of the resulting solution, dilution thereof with water with the addition of a stabilizing agent-citric acid or salts thereof, followed by neutralization of the solution and drying, and containing the following components, percent by weight:
   calcium—2–6,
   sodium—19–23,
   potassium—0.04–0.18,
   mineral acid anion—6–10.6,
   orthophosphoric acid anion—1.5–5.0,
   water-soluble proteins—1.0–5.0,
   magnesium—0.05–0.2,
   mixture of trace elements including fluorine, tin, manganese, zinc, iron—0.01–0.02
   complex citrate compounds as calculated for citric acid anion—the balance,
and having the following proportions of the starting components, percent by weight:
   tartaric acid—11–15,
   foaming agent—1.8–2.27,
   sodium bicarbonate—42–46,
   binder—0.11–0.13,
   flavouring agent—0.8–1.2,
   anti-caries substance—1–6,
   abrasive substance—the blance.

2. A treatment-and-prophylactic dental preparation as claimed in claim 1, wherein sodium sulphate is additionally contained in an amount of from 1.9 to 2.1 percent by weight in order to ensure a long-time storage.

3. A treatment-and-prophylactic dental preparation as claimed in claim 1, wherein as the abrasive substance use is made of dicalciumphosphate dihydrate.

* * * * *